United States Patent
Di Lelio et al.

[19]

[11] Patent Number: 5,902,337
[45] Date of Patent: May 11, 1999

[54] VALVED BLADDER PROSTHESIS

[75] Inventors: Alessandro Di Lelio, Montevecchia; Francesco Minoletti, Turin, both of Italy

[73] Assignee: Biomedica Sviluppo Srl, Milan, Italy

[21] Appl. No.: 08/913,959

[22] PCT Filed: Apr. 3, 1996

[86] PCT No.: PCT/EP96/01458

§ 371 Date: Nov. 25, 1997

§ 102(e) Date: Nov. 25, 1997

[87] PCT Pub. No.: WO96/31173

PCT Pub. Date: Oct. 10, 1996

[30] Foreign Application Priority Data

Apr. 6, 1995 [IT] Italy ................................ MI95A0699

[51] Int. Cl.[6] ...................................................... A61F 2/04
[52] U.S. Cl. ........................ 623/12; 600/30; 128/DIG. 25
[58] Field of Search ................................... 623/8, 11, 12; 600/30, 31; 128/DIG. 25

[56] References Cited

U.S. PATENT DOCUMENTS

| | | | |
|---|---|---|---|
| 3,575,158 | 4/1971 | Summers | 623/12 |
| 3,953,897 | 5/1976 | Chevallet et al. | 623/12 |
| 4,044,401 | 8/1977 | Guiset | 623/12 |
| 4,228,550 | 10/1980 | Salkind | |
| 4,976,735 | 12/1990 | Griffith et al. | 623/12 |
| 5,041,136 | 8/1991 | Wascher et al. | |
| 5,108,430 | 4/1992 | Ravo | 623/11 |

FOREIGN PATENT DOCUMENTS

| | | |
|---|---|---|
| 2 116 838 | 7/1972 | France . |
| 2 255 877 | 7/1975 | France . |
| WO 93/16659 | 9/1993 | WIPO . |

*Primary Examiner*—Mickey Yu
*Assistant Examiner*—Bruce E. Snow
*Attorney, Agent, or Firm*—Evenson, McKeown, Edwards & Lenahan, P.L.L.C.

[57] ABSTRACT

A bladder prosthesis having a silicone bag with radiused lower corners and a band of anchoring fabric at the upper side, the fabric being densely looped to allow body tissue ingrowth to hold the artificial bladder in place. For entry of the urine into the bladder and emptying thereof, the bladder has in its lower part a valve communicating with a funnel-shaped conduit. The valve includes an adapter with fittings for connection to nephrostomic catheters, a valve body contained inside the adapter and having urine inlet and outlet openings and a deformable diaphragm-type elastic valve member to open and close the communication between the inside of the artificial bladder and the inside of the valve body.

11 Claims, 3 Drawing Sheets

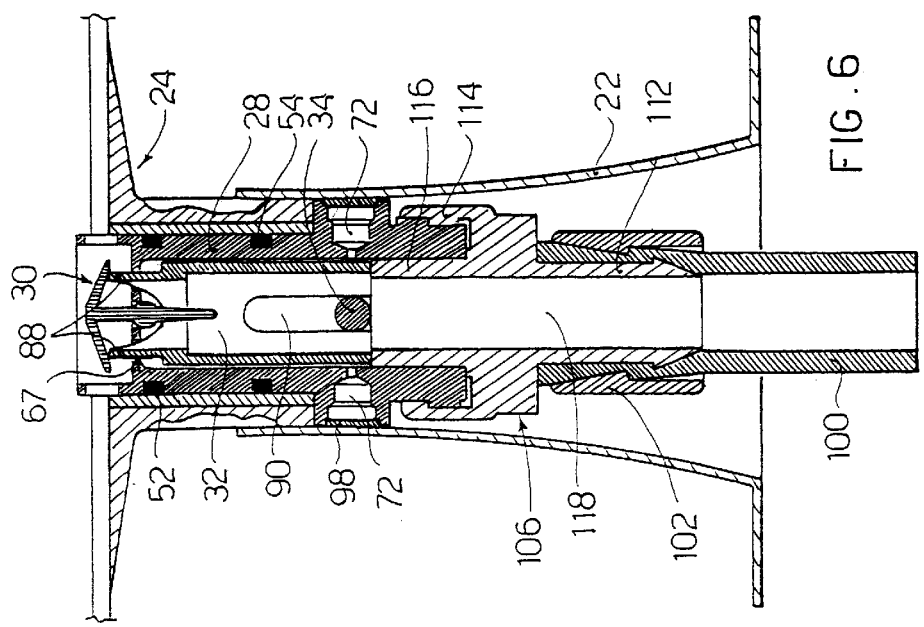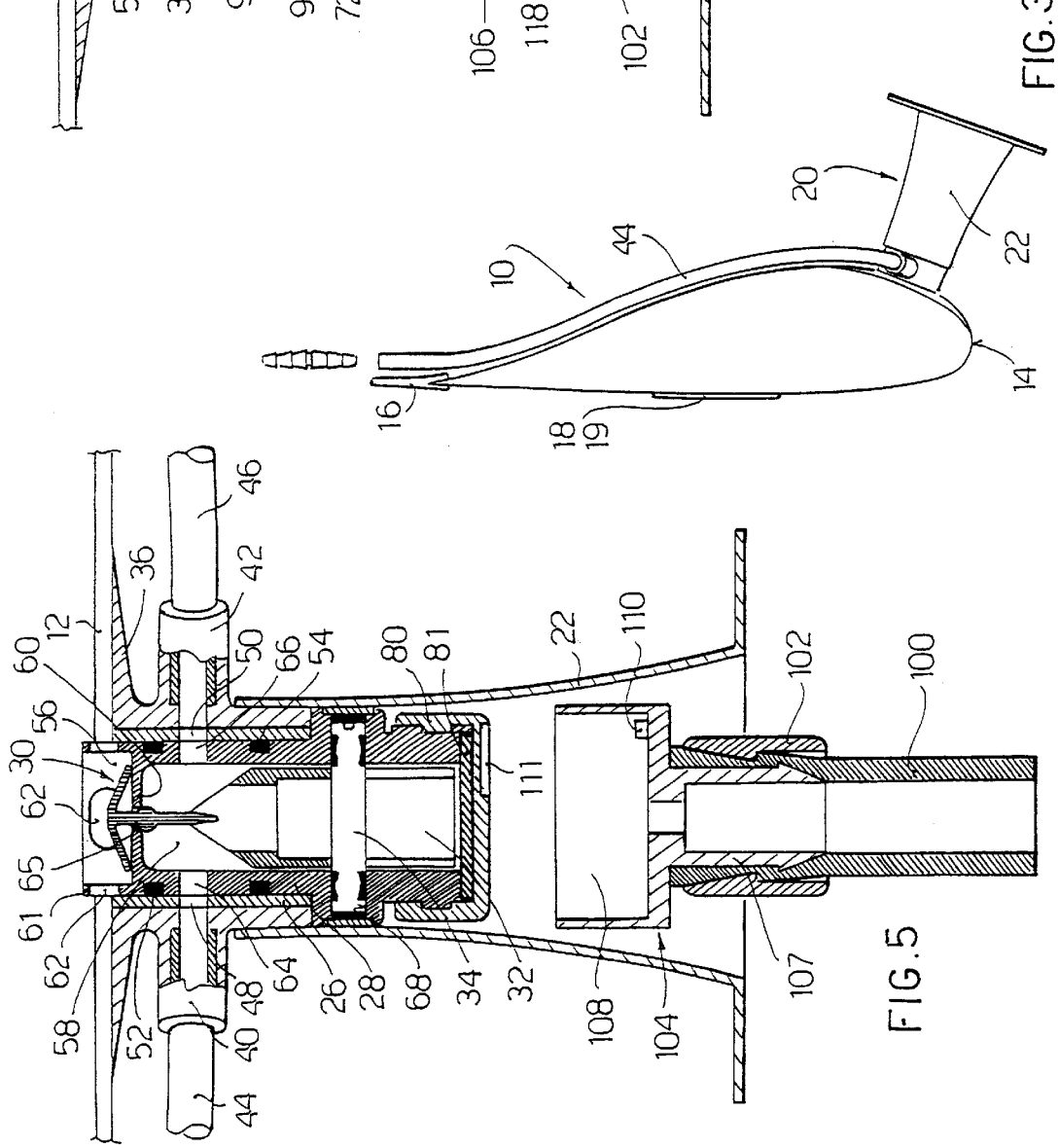

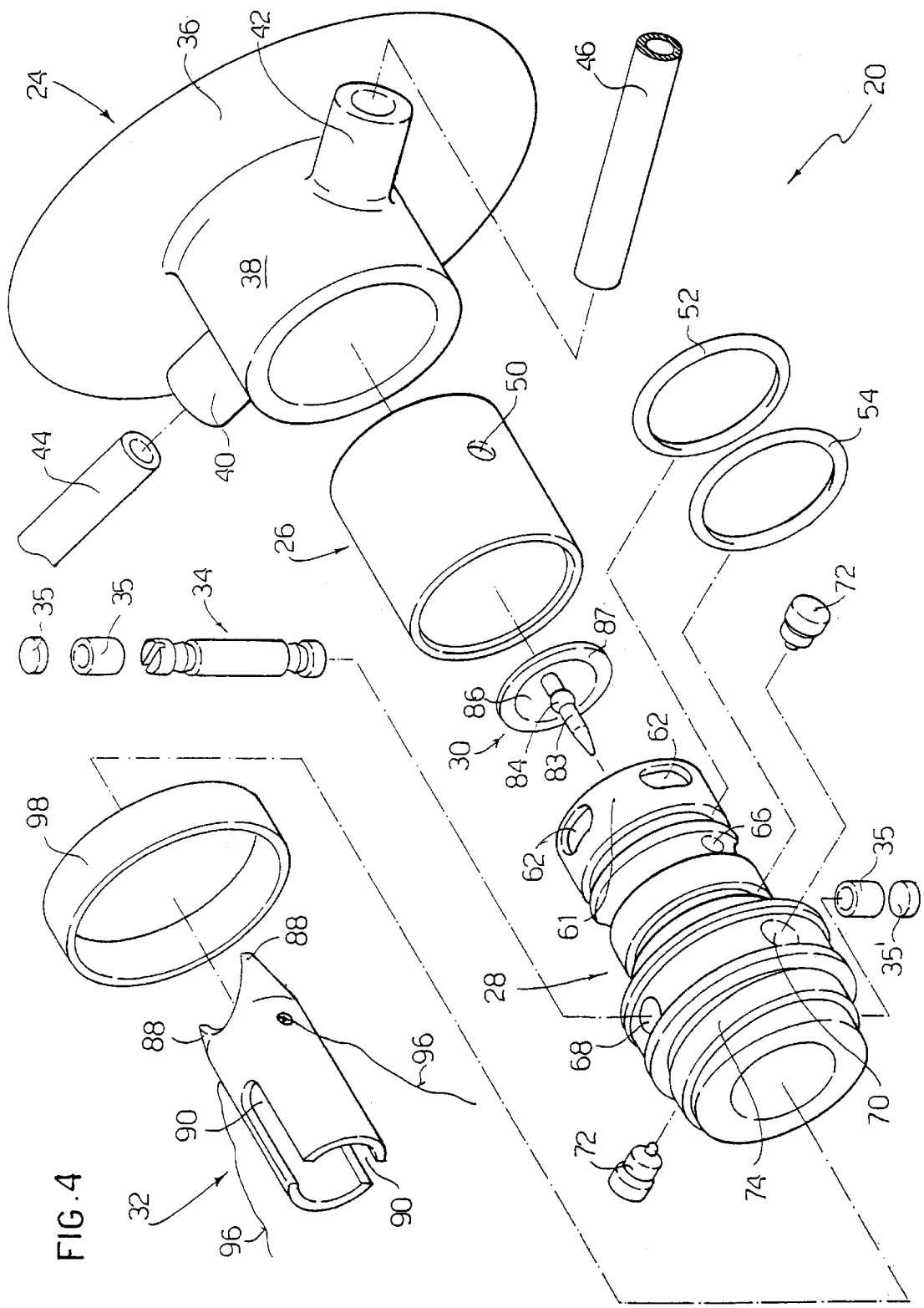

VALVED BLADDER PROSTHESIS

BACKGROUND AND SUMMARY OF THE INVENTION

A number of procedures are known for the treatment of obstructive nephropathies, that is to say that type of condition that results in obstructed flow of use from the kidney to the outside, due to tumours or other causes.

These can be divided into surgical and interventional procedures. The former consist of forming an external aperture for the ureter, or for the ureters in the case of bilateral obstruction, through a vast range of surgical procedures; either directly (cutaneous ureterostomy) or by means of variously used bowel loops. The latter, on the other hand, make use of catheters which, by different routes, can be inserted percutaneously directly into the kidney (nephrostomic catheters), inducing drainage of the urine to the outside, or into the ureter (ureteral stent) passing through the stenotic area and re-establishing the communication between the portion upstream and downstream of the obstruction, thus allowing urinary outflow. Nephrostomic catheters are connected to urine collection bags worn on the outside of the patient's body that are emptied when they are fill. These bags are made of plastic material, for example PVC, and are substantially rectangular in shape, with a tube for connection to the nephrostomic catheter and in some cases also an emptying tube.

Nephrostomic catheters have the drawback of requiring maintenance and medication at the fixing point. Moreover, the fixing system through suturing to the skin or by self-anchoring means forming part of the catheter, often loosens allowing the catheter to become dislodged. Moreover, the presence of the urine collection bag causes inconvenience to the patient, besides causing a feeling of disability in patients already psychologically tried by a long illness.

Ureteral stents overcome the above problems but require that it be possible to pass the obstruction, something which cannot always be done.

The aim of the present invention is to overcome the practical and psychological drawbacks due to the need to wear an external urine collection bag. A further aim is to provide a prosthesis that can be worn by the patient for a long time without problems.

Another aim is to allow the contents of the prosthesis to be emptied easily. Yet another aim is to provide a prosthesis many parts of which can be easily dismantled for cleaning and sterilisation and which allows easy access to the other parts, for example to nephrostomic catheters, for cleaning.

Said drawbacks have been overcome by means of an assembly comprising a bag element, at least one type of band material and a valve element.

The prosthesis herein described has been conceived to replace the natural bladder in its role as a reservoir and in controlling discharge of accumulated fluid.

The bladder prosthesis is made of strong elastic material, is shaped so as to be accommodated in the median hypogastric region, in a subcutaneous, prefascial site or pocket where it is positioned after incising the skin along the subumbilical transiliac line and then freeing the integuments down to the suprapubic region.

The shape is roughly comparable to a rectangle with two corners, those belonging to one of the longer sides, strongly radiused.

This longer side forms the bottom part of the bladder whilst the opposite side is intended to be anchored to the muscle fascia initially by suturing and subsequently by incorporation into the reactive fibrous tissue of a biocompatible material fixed to the bag for this purpose. The bladder is preferably a thin silicone bag obtained by spraying on a model silicone material dispersed in solvent then evaporated, and then curing in a high-temperature oven; or by dipping/brushing a model into/with silicone material dispersed in solvent.

The silicone bag could be obtained by whichever other known way apt for generating an opportune thickness of the biocompatible and elastic material.

A silicone-metal-plastic structure is applied in the central part of the lower side, constituting the inlet and outlet valve of said bladder. Two lengths of silicone tube for connection with the ends of two nephrostomic catheters converge on this structure. Under the pressure of the fluid coming from the catheters, the valve opens so that the urine can flow into the bladder. Emptying of the bladder takes place through said valve.

This arrangement makes it possible to optimise the maximum size of the discharge outlet and at the same time the minimum pressure for opening of the valve for filling.

Lastly a plug provided with a gasket ensures tight closure of the bladder throughout the day.

The valve that is described also serves to stop fluid pressure waves, pulsed or otherwise, from the bladder towards the kidneys. In fact any reflux that might occur from the bladder to the kidneys through the nephrostomic catheters because of a defective valve seal would create a pressure wave that would oppose the hydrostatic filtering pressure of the urine, and would therefore injure the kidneys structures capable to secrete urine.

BRIEF DESCRIPTION OF THE DRAWINGS

The subject of the invention and the inherent advantages will be clearer on reading the detailed description that follows of a non-limiting exemplary embodiment thereof with reference to the attached drawings in which:

FIG. 3 is a side view of the bladder prosthesis, from the left in FIG. 1;

FIG. 4 is an exploded perspective view, on an enlarged scale, of the valve of the prosthesis according to the invention;

FIG. 5 is a section of the valve along a plane containing its longitudinal axis; the entrances for the catheters are illustrated with their axes in said plane for clarity's sake, even if this is not a faithful representation; the valve is in the closed state, that is to say closed to the outside but with access possible for the urine coming from the nephrostomic catheters; a device for opening and removing the plug is illustrated in section in the same figure;

FIG. 6 is a section of the valve along an axial plane like FIG. 5, illustrated when forced open for emptying, with the opening device and emptying channel applied.

DETAILED DESCRIPTION OF THE INVENTION

Figure 1:
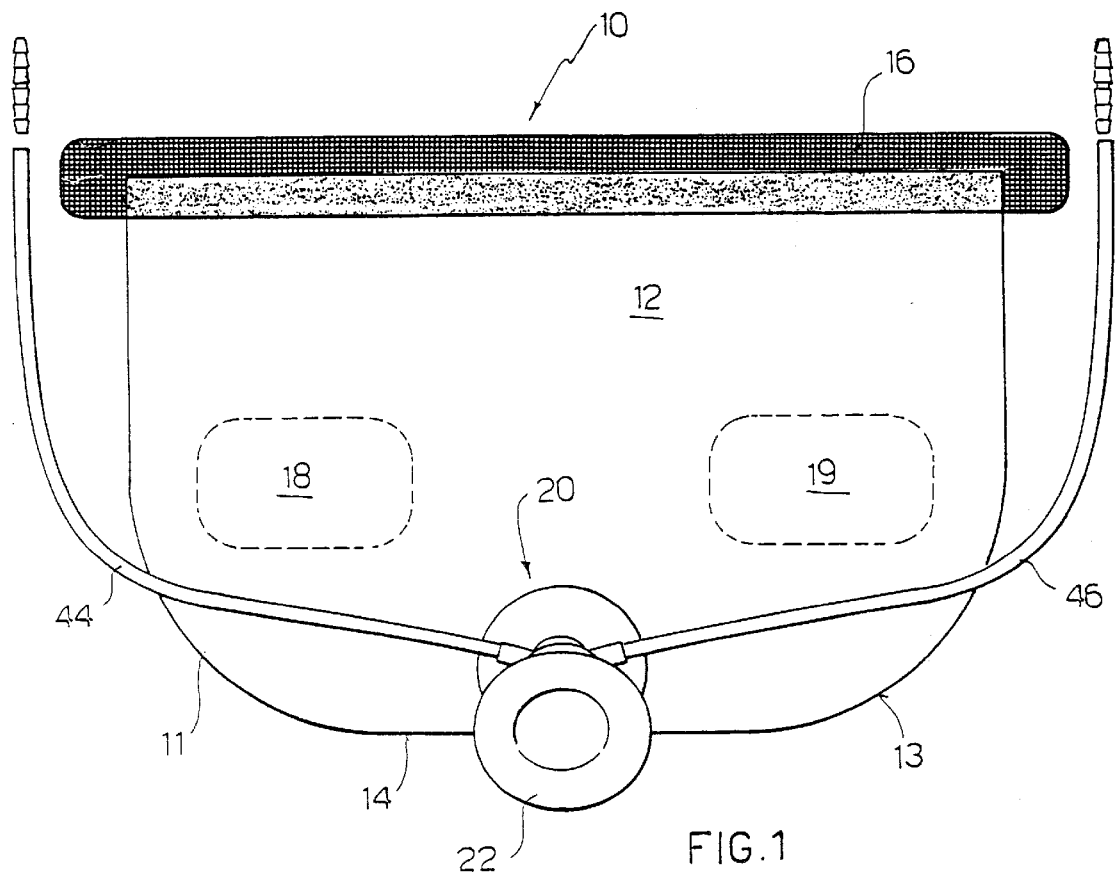
FIG. 1 shows a front elevational view, on a reduced scale, of a bladder prosthesis according to the present invention.
Figure 2:
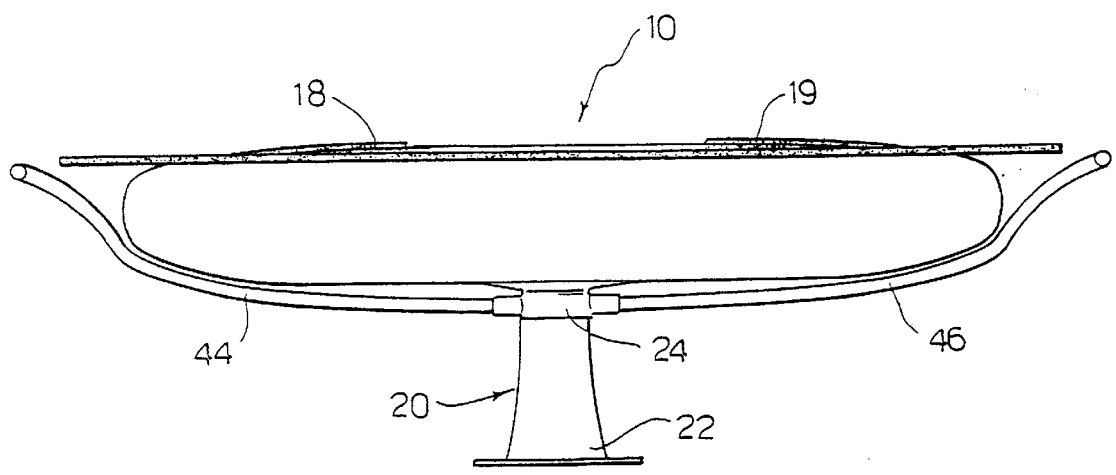
FIG. 2 is a top view of the prosthesis in FIG. 1.

As can be seen, in FIGS. 1 and 3, a bladder prosthesis according to the invention, indicated as a whole by reference number 10, comprises a bag 12 made of flexible biocompatible material, with the bottom corners 11, 13 rounded when viewed from the front, as can be observed in FIG. 1, and a rounded bottom edge 14, as can be observed in FIG. 3. A band of biocompatible fabric is applied to the upper sealed edge, with a looped weave such as to promote ingrowth of body tissue in order to incorporate it. The band is indicated by reference number 16. Further portions of biocompatible anchoring fabric can be disposed on the surface of the bag, for example as on the areas indicated by 18 and 19 in the figures. A filing and emptying valve, indicated as a whole by reference number 20, is applied in proximity to the lower edge of the bag and co-operates with a funnel-shaped conduit 22. The bag is preferably made of thin silicone, obtained by spraying silicone material dispersed in solvent, then evaporated, and is then cured in an oven at high temperature. The bag, however, can be obtained in whichever other known way or in a way within the reach of a skilled person. A preferred material for the bag is a MEDICAL GRADE silicone. The measurements of the bag are preferably 200×130×40 mm, with a proper wall thickness. The band 16 and bands 18 and 19 if used are preferably made of a Dacron (Dupont de Nemours trademark). Fabric woven in a special per se known manner to obtain a surface dense with loops of thread, within which tissue growth can take place for final stabilisation of the prosthesis.

The valve 20 will now be described in greater detail with reference to FIGS. 4, 5 and 6. It comprises an adapter 24, a positioning cylinder 26, a valve body 28, a mushroom-type open-close or shutter valve member 30, and a pusher element 32 guided by a transverse guide pin 34.

The adapter is an element made of flexible material shaped with a thin-walled widened head, indicated by 36, applied in any per se known manner to the bottom wall of the bag 12, around an aperture in it (not shown). The adapter 24 further comprises a cylindrical part or coupling sleeve 38 into which connections or entrances 40 and 42 for nephrostomic catheters open, said connections preferably being disposed so that the angle between them is slightly less than 180°. The nephrostomic catheters are indicated with reference numbers 44, 46 and are made of flexible, biocompatible, tubular material Since said catheters are of any per se known type, they will not be described in greater detail, here. Within the cylindrical part 38 of the adapter is contained the relatively rigid positioning cylinder 26, provided with holes 48, 50 in its skirt portion, said holes being in positions coinciding with the connections 40, 42 for the catheters, in the adapter. The valve body 28 is housed in an inner chamber defined by cylinder 26 and is closed tight against said cylinder 26 by means of two O-rings, indicated respectively by 52, 54, accommodated in seats on the outer surface of the valve body, on opposite sides with respect to the openings 48, 50. The valve body has an end chamber or chamber for the open-close valve member, indicated by 56, and a valve chamber or pusher chamber, indicated by 58, between which chambers extends a perforated portion or septum 60. The chamber 56 for the valve-member is defined by a cylindrical outer wall 61 with peripheral openings 62. The pusher chamber 58 has inlet openings 64, 66 in register with the connections 40, 42 for the catheters in the adapter. Partition 60 has a central opening 65 and side openings 67. The valve body also has further through openings 68, 68 and 70, 70 with axes at right angles to each other. The openings 68, 68 accommodate the ends of the pusher guide pin 34, whilst the openings 70 accommodate plugs 72, 72, the function of which will be described below. An end part of the valve body is shaped with a screw thread 74 or other engaging means, to releasably engage a cap or cap 80 (shown in FIG. 5) which closes the chamber 58 with a tight seal by means of a gasket 81.

The valve body accommodates a stem of valve member 30 in the opening 65. Said valve member is mushroom-shaped with a stem 83 having a bulge 84 in an intermediate position and an enlarged cap or diaphragm portion 86, said cap preferably having a frusto-conical or tapered shape, with an edge or lip 87 having an external diameter sufficient to completely cover openings 67. Member 30 is inserted into opening 65 so that a part of its stem remains inside it with the bulge 84 on one side of partition 60 and the tapered widened partition 86 on the other side. The valve body also accommodates the pusher 32, which is substantially cylindrical in shape with two diametrically opposed operating protrusions 88, 88, spaced from each other and sized as to be able to pass through openings 67 of the partition, 60, and also has opposed guide grooves 90, 90, substantially of the same or a slightly greater width than the diameter of guide pin 34 and engaged on it, so that the pusher can slide axially with respect to the valve body, and be guided by said pin arranged transversally therein. The pusher has elastic return cords 96, tied to the valve body by means of the above-mentioned plugs 72, 72. The guide pin is preferably mounted on the valve body by means of cylindrical gaskets 35 or with end plugs 35' and a retaining ring 98 is arranged around the ends of said pin and the plugs.

According to the invention a valve opening device is also provided, comprising a cap unscrewing element and a pushing element to open the valve member, said elements preferably being interchangeable on a handle having a channel that can also serve as an emptying channel. This accessory device is shown in FIGS. 5 and 6 in sectional view along the axis of the emptying channel element, and will be, described below. The device thus comprises an emptying channel and handle element conduit, indicated by 100, a locking ring 102, a cap engaging element 104 and a pushing and discharge element 106 for the pusher (FIG. 6). The cap engaging element has a shank 107 that can be engaged in the conduit 100, a cup-shaped part 108 and a projection 110 designed to be engaged in a radial groove or hollow 111 on the bottom of cap 80. It will be seen that by arranging the cup-shaped part 108 around cap 80 so that projection 110 engages the hollow 111 and turning the conduct 100 which is accessible from the outside, it is possible to unscrew cap 80. Once cap 80 has been unscrewed, it is possible to apply pushing and discharge element 106 to element conduit 100, said pushing and discharge element 106 comprising an attachment shank 112, a cup-shaped part 114 that can be screwed onto the thread of the valve body, and an inner cylindrical pushing part 116, all these parts defining a through channel 118.

The operation of the prosthesis will now be described.

The urine coming from the kidneys is conveyed inside the valve body 28 through the nephrostomic catheters 44, 46.

Here the fluid could take two different opposite routes, but one, the one communicating with the outside, is functionally sealed, at this stage, by the suitably tightened, threaded cap 80.

The second route is towards the reservoir or bladder bag 12, to reach it has to pass through the valve lumen proper, formed by openings 65, 67. The silicone valve member 30 presses on the edges of the valve body partition with the retaining lip 87, creating a tight seal against the passage of fluids up to a certain head pressure. The diaphragm 86 is held elastically in a closed position by means of a force inherent in the shape and material of valve member 30 and/or imparted by an elastic element (for example a thin cable—not shown) which exerts its force, preferably adjustable, parallel to the valve axis.

When the force due to the pressure exerted on the undersurface of the valve diaphragm by the urine coming from the catheters exceeds the force due to the elasticity of the materials, the fluid enters the bladder and begins to fill it.

This mechanism operates whether the patient remains in an upright or a supine position.

Obviously, the pressure within the bladder increases as the bladder fills, putting up an increasing resistance to entry of the fluid.

Once the bladder is full the pressure of the fluid from the catheters will no longer be sufficient to overcome the resistance of the valve member and the inflow of urine will therefore stop.

To completely empty the prosthesis bag, it is sufficient to unscrew the plug 80. As soon as this is removed there is a slight limited discharge of fluid. This small amount is that always present in the valve body, coming directly from the catheters.

With the bladder bag completely or partially filled, its internal pressure is greater than the external pressure (which coincides with that of the valve body) therefore the mushroom-shaped diaphragm continues to adhere firmly to the passage section.

In order to remove said diaphragm from its perfectly sealed position, the pushing and discharge element 106 with the handle conduit 100 is screwed onto the valve body.

This connection raises the pusher element 32 which thus raises the mushroom-shaped diaphragm with the points 88 (FIG. 6), allowing the fluid in the bag 12 to pass through valve 20 to the conduit 100 and to the outside.

If, before emptying is complete, the connection is removed (by unscrewing it), the system of unbalanced pressures immediately re-establishes the tight seal of the bladder, interrupting the flow. The emptying operation nevertheless ends regularly when there is no fluid in the bladder.

Removal of the pushing and discharge element 106 in any case causes the return of the diaphragm to the position in which the filling-emptying lumen is sealed, the diaphragm being returned to that position by elastic force, and the return of the pusher to the situation in FIG. 5, because of the elastic cords 96.

Once emptying has been carried out the screw plug is again fitted.

The funnel-shaped conduit that serves to prevent emptying in unwanted directions can be cleaned, dried, washed and lastly folded beneath the clothes.

It will be appreciated that the valve body with the pusher and attachments can easily be periodically removed for cleaning. With the valve body removed the catheters can also be accessed for cleaning with a swab and/or cleaning fluid can be introduced into the bag.

We claim:

1. A bladder prosthesis assembly for subcutaneous implantation, comprising a bag element made of biocompatible material;
    at least one band of material on said bag element suitable for facilitating fixing to body tissue;
    a valve element for inlet/outlet of urine to/from the bag element, said valve element being connected at a lower part of the bag element around an open therein and comprising connections for nephrostomic catheters, wherein the valve element comprises an adapter having a coupling sleeve with said connections for nephrostomic catheters, a valve body at least partially disposed in the adapter, with a tight seal, the valve body having openings in register with said catheter connections on the adapter, a first chamber communicating with said openings and delimited from the bag element by a perforated partition having a passage therethrough, a valve member being provided on the valve body and moveable between a condition in which a peripheral lip of the valve member thereof seals the passage through the partition, and a condition in which it leaves said passage free, and a removable plug or cap to close said valve body with a tight seal at an end thereof opposite to the partition.

2. A bladder prosthesis assembly according to claim 1 wherein it comprises one said band in a position along an upper edge of the bag and further band portions of said material on the bag.

3. A bladder prosthesis assembly according to claim 1 wherein the bag is made of strong, flexible, elastic material and the at least one band of material is made of material suitable to promote tissue growth in order to fix the bladder prosthesis assembly firmly.

4. A bladder prosthesis assembly according to claim 1, wherein the valve body further comprises a second chamber separated from the first chamber by the perforated partition.

5. A bladder prosthesis assembly according to claim 4, further comprising a pusher element in said valve chamber, said pusher element being axially moveable in the valve chamber between a retracted position, in which it does not act on the diaphragm-type valve member, and an extended position, in which it acts with points thereof on the valve member through at least one opening in the partition, said pusher being elastically returned to the retracted or resting position.

6. A bladder prosthesis assembly according to claim 5, wherein said pusher is engaged with a transversal guide element in the valve body, to guide the movement between the retracted and extended position.

7. A bladder prosthesis assembly according to claim 5, further comprising an elastic means connected to the diaphragm-type valve member to return it to the closed position.

8. A bladder prosthesis assembly according to claim 5 further comprising a pushing and discharge element, said element comprising a sleeve or cylindrical pushing part of a suitable size to be accommodated in the valve body and extending axially sufficiently to push the pusher element against the diaphragm to open passages in the valve body partition, and comprising a through channel, and in that it further comprises a handle-and-channel element connectable to said pushing-and-discharge element, for allowing fluid to pass.

9. A bladder prosthesis assembly according to claim 1 wherein said valve member comprises an attachment stem and a mushroom-shaped diaphragm made of elastic material, said valve member being essentially undeformed in the closed condition, whilst in said open condition it is substantially elastically deformed.

10. A bladder prosthesis assembly according to claim 1, further comprising a device to unscrew said cap, said device comprising a handle and a cap engaging element, removably attached to said handle.

11. A bladder prosthesis assembly according to claim 1, further comprising a funnel-shaped conduit located on the valve element.

* * * * *